US012356909B2

(12) United States Patent
Aarden et al.

(10) Patent No.: US 12,356,909 B2
(45) Date of Patent: *Jul. 15, 2025

(54) TOMATO PLANTS WITH IMPROVED TRAITS

(71) Applicant: Seminis Vegetable Seeds, Inc., St. Louis, MO (US)

(72) Inventors: Harriette C. Aarden, South Holland (NL); Bernardus van den Bosch, Zoetermeer (NL); Bart Willem Brugmans, Beek en Donk (NL); Benjamin C. Hunter, Zuid-Holland (NL); Rose Iris R. Rehrig, Marina, CA (US); Maria F. Rodriguez, St. Paul, MN (US); Bram Rozier, Zuid-Holland (NL); Alberto Vecchietti, Milan (IT); Ruth A. Wagner, Chesterfield, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 132 days.

This patent is subject to a terminal disclaimer.

(21) Appl. No.: 17/224,021

(22) Filed: Apr. 6, 2021

(65) Prior Publication Data

US 2021/0324395 A1  Oct. 21, 2021

Related U.S. Application Data

(62) Division of application No. 16/239,405, filed on Jan. 3, 2019, now Pat. No. 11,001,851.

(60) Provisional application No. 62/613,617, filed on Jan. 4, 2018.

(51) Int. Cl.
| | |
|---|---|
| *A01H 5/08* | (2018.01) |
| *A01H 1/00* | (2006.01) |
| *A01H 1/04* | (2006.01) |
| *A01H 6/82* | (2018.01) |

(52) U.S. Cl.
CPC .............. *A01H 1/04* (2013.01); *A01H 1/00* (2013.01); *A01H 5/08* (2013.01); *A01H 6/825* (2018.05)

(58) Field of Classification Search
None
See application file for complete search history.

(56) References Cited

U.S. PATENT DOCUMENTS

| 11,641,841 B2 | 5/2023 | van den Bosch |
| 2016/0100538 A1 | 4/2016 | Aarden et al. |

FOREIGN PATENT DOCUMENTS

| WO | 2016044632 | 3/2016 |
| WO | 2017174727 A1 | 10/2017 |

OTHER PUBLICATIONS

Alseekh, et al., "Resolution by Recombination: Breaking Up Solanum Pennellii Introgressions," Trends in Plant Science 18(10):536-538 (2013).
Baxter, et al., "Comparison of Changes in Fruit Gene Expression in Tomato Introgression Lines Provides Evidence of Genome-Wide Transcriptional Changes and Reveals Links to Mapped QTLs and Described Traits," Journal of Experimental Botany 56(416):1591-1604 (2005).
Causse, et al., "A Genetic Map of Candidate Genes and QTLs Involved in Tomato Fruit Size and Composition," Journal of Experimental Botany 55(403):1671-1685 (2004).
Eshed and Zamir, "An Introgression Line Population of Lycopersicon Pennellii in the Cultivated Tomato Enables the Identification and Fine Mapping of Yield-Associated QTL," Genetics 141(3):1147-1162 (1995).
Eshed and Zamir, "Introgressions from Lycopersicon pennellii Can Improve the Soluble-Solids Yield of Tomato Hybrids," Theoretical and Applied Genetics 88(6-7):891-897 (1994).
Eshed and Zamir, "Less-than-Additive Epistatic Interactions of Quantitative Trait Loci in Tomato," Genetics 143(4):1807-1817 (1996).
Tieman, et al., "A Chemical Genetic Roadmap to Improved Tomato Flavor," Science 355(6323):391-394 (2017).
International Search Report and Written Opinion regarding International Application No. PCT/US2019/012169, mailed May 8, 2019, 13 pages.
Steinhauser et al., "Identification of Enzyme Activity Quantitative Trait Loci in a Solanum lycopersicum x Solanum pennellii Introgression Line Population", Plant Physiology, 2011, 157:998-1014.
GenBank Accession No. HG975513, Nov. 17, 2015.
Extended European Search Report regarding European App. No. 19735965.6, dated Aug. 3, 2021.
U.S. Appl. No. 17/464,640, filed Sep. 1, 2021, van den Bosch.
U.S. Appl. No. 18/128,598, filed Mar. 30, 2023, van den Bosch.

*Primary Examiner* — Phuong T Bui
(74) *Attorney, Agent, or Firm* — Dentons US LLP

(57) ABSTRACT

Tomato plants exhibiting fruit with increased BRIX content are provided, together with methods of producing, identifying, or selecting plants or germplasm with an increased BRIX phenotype and lacking undesirable leaf necrosis. Such plants include tomato plants comprising introgressed genomic regions conferring increased BRIX without necrosis. Compositions, including novel polymorphic markers for detecting plants comprising introgressed alleles providing increased BRIX without necrosis, are further provided.

3 Claims, 1 Drawing Sheet

Specification includes a Sequence Listing.

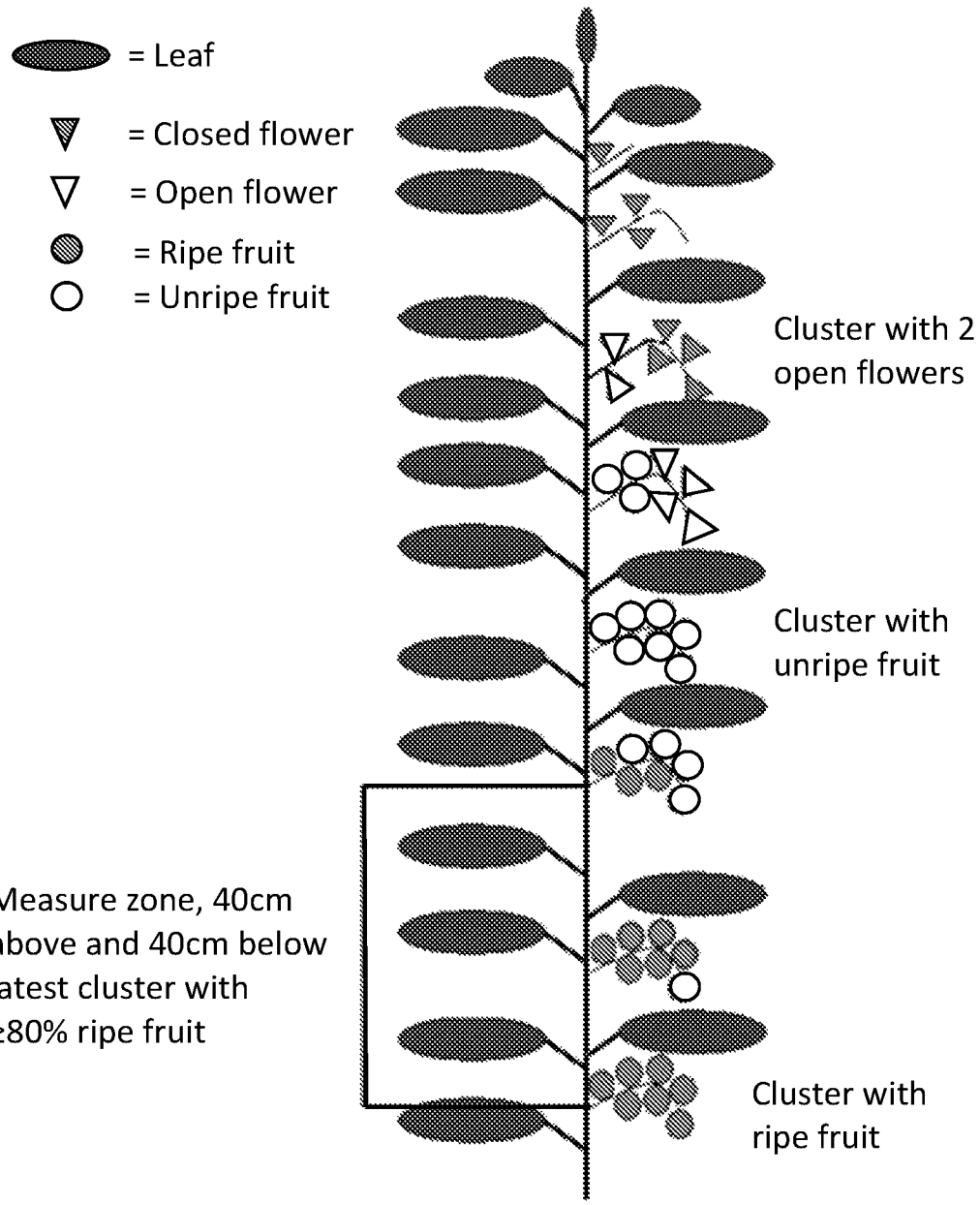

TOMATO PLANTS WITH IMPROVED TRAITS

CROSS-REFERENCE TO RELATED APPLICATIONS

This application is a divisional of U.S. patent application Ser. No. 16/239,405, filed Jan. 3, 2019, now U.S. Pat. No. 11,001,851, which claims the priority of U.S. Provisional Appl. Ser. No. 62/613,617, filed Jan. 4, 2018, each of which is incorporated herein by reference in its entirety.

INCORPORATION OF SEQUENCE LISTING

A sequence listing containing the file named "SEMB033US_ST25.txt" which is 36 kilobytes (measured in MS-Windows®) and created on Jan. 2, 2019, and comprises 65 sequences, is incorporated herein by reference in its entirety.

FIELD OF THE INVENTION

The present invention relates to the field of plant breeding and more specifically to methods and compositions for producing tomato plants exhibiting improved fruit quality without linked deleterious traits.

BACKGROUND

Fruit quality and flavor are important traits in tomato breeding, particularly for the development of commercial varieties. Although fruit quality alleles have been identified in tomato, efforts to introduce these alleles into cultivated lines have been hindered by a lack of specific markers linked to the alleles, as well as the presence of deleterious alleles genetically linked to fruit quality alleles that lead to unacceptable plant traits such as leaf necrosis. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an often incomplete understanding of the genetic background underlying expression of a desired phenotype. In the absence of accurate and validated markers for use in MAS, it may not be feasible to produce new plant lines exhibiting a certain fruit quality without unacceptable necrosis.

SUMMARY

In a first aspect, Solanum lycopersicum a plant is provided comprising a recombinant chromosomal segment on chromosome 1, wherein said chromosomal segment comprises an introgressed BRIX allele from S. pennellii conferring increased BRIX to the fruit of said plant compared to the fruit of a plant not comprising said allele, and wherein said chromosomal segment lacks a deleterious allele genetically linked to said BRIX allele that confers necrosis to said plant when present. In certain embodiments, said BRIX allele is located within a chromosomal segment flanked by marker locus M3 (SEQ ID NO:11) and marker locus M11 (SEQ ID NO:51) on chromosome 1 of said plant, for example within a chromosomal segment flanked by marker locus M3 (SEQ ID NO:11) and marker locus M9 (SEQ ID NO:41) on chromosome 1 of said plant, or within a chromosomal segment flanked by marker locus M4 (SEQ ID NO:16) and marker locus M5 (SEQ ID NO:21) on chromosome 1 of said plant. In some embodiments, said recombinant chromosomal segment comprises a marker locus selected from the group consisting of M1 (SEQ ID NO:1), M2 (SEQ ID NO:6), M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), M10 (SEQ ID NO:46), M11 (SEQ ID NO:51), M12 (SEQ ID NO:56), and M13 (SEQ ID NO:61) on chromosome 1. In further embodiments, said plant comprises an S. lycopersicum allele at marker locus M2 (SEQ ID NO:6) and an S. pennellii allele at marker locus M3 (SEQ ID NO:11). In yet further embodiments, said plant comprises an S. pennellii allele at marker locus M9 (SEQ ID NO:41), and an S. lycopersicum allele at marker locus M10 (SEQ ID NO:46). Further provided are plants comprising an S. lycopersicum allele at M2 (SEQ ID NO:6) and M10 (SEQ ID NO:46) and an S. pennellii allele at a marker locus selected from the group consisting of M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), and M12 (SEQ ID NO:56). In some embodiments, said BRIX allele is located within a chromosomal segment in the genome of said plant flanked by 96,871,421 bp and 98,155,761 bp on the Tomato SL3.0 map. Further provided are plant parts of plant disclosed herein. In certain embodiments, said introgressed BRIX allele is derived from a plant of S. pennellii line LA0716.

In another aspect, a recombinant DNA segment is provided comprising a BRIX allele that confers increased BRIX to the fruit of a plant, and lacking a deleterious allele genetically linked to said BRIX allele that confers necrosis to a plant. In some embodiments, said recombinant DNA segment comprises a sequence selected from the group consisting of M1 (SEQ ID NO:1), M2 (SEQ ID NO:6), M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), M10 (SEQ ID NO:46), M11 (SEQ ID NO:51), M12 (SEQ ID NO:56), and M13 (SEQ ID NO:61). In further embodiments, recombinant DNA segments disclosed herein are comprised within a plant, plant part, plant cell, or seed, and said DNA segment may confer increased BRIX to the fruit of said plant.

In yet another aspect, methods are provided of producing a tomato plant exhibiting fruit with increased BRIX, comprising: a) crossing the tomato plant disclosed herein with itself or with a second tomato plant of a different genotype to produce one or more progeny plants; and b) selecting a progeny plant comprising said BRIX allele and lacking said deleterious allele. In certain embodiments, selecting said progeny plant comprises detecting an S. Lycopersicum allele at M2 (SEQ ID NO:6) and detecting an S. pennellii allele at M3 (SEQ ID NO:11). In further embodiments, selecting said progeny plant further comprises detecting an S. pennellii allele at marker locus M9 (SEQ ID NO:41), and detecting an S. lycopersicum allele at marker locus M10 (SEQ ID NO:46). In further embodiments, said progeny plant is an $F_2$-$F_6$ progeny plant. In yet further embodiments, producing said progeny plant comprises backcrossing.

In a further aspect, methods are provided of producing a tomato plant exhibiting fruit with increased BRIX, comprising introgressing into a plant a BRIX allele within a recombinant chromosomal segment flanked in the genome of said plant by marker locus M3 (SEQ ID NO:11) and marker locus M11 (SEQ ID NO:51) on chromosome 1, wherein said BRIX allele confers increased BRIX to said fruit of said plant compared to a plant not comprising said allele, and wherein said recombinant chromosomal segment lacks a deleterious allele genetically linked to said BRIX allele that confers increased necrosis to said plant when present. In some embodiments, said recombinant chromosomal segment is located within a chromosomal segment flanked by marker locus M3 (SEQ ID NO:11) and marker locus M9 (SEQ ID NO:41) on chromosome 1 of said plant, for example within a chromosomal segment flanked by marker locus M4 (SEQ ID NO:16) and marker locus M5 (SEQ ID NO:21) on chromosome 1 of said plant. In certain embodiments, said recombinant chromosomal segment comprises a marker locus selected from the group consisting of M1 (SEQ ID NO:1), M2 (SEQ ID NO:6), M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), M10 (SEQ ID NO:46), M11 (SEQ ID NO:51), M12 (SEQ ID NO:56), and M13 (SEQ ID NO:61). In further embodiments, said plant comprises an *S. lycopersicum* allele at marker locus M2 (SEQ ID NO:6) and an *S. pennellii* allele at marker locus M3 (SEQ ID NO:11). In yet further embodiments, said plant comprises an *S. pennellii* allele at marker locus M9 (SEQ ID NO:41), and an *S. lycopersicum* allele at marker locus M10 (SEQ ID NO:46). In methods provided herein, introgressing may comprise backcrossing, marker-assisted selection, or assaying said fruit of said plant for increased BRIX. Further provided are tomato plants obtainable by the methods provided herein.

In yet a further aspect, methods are provided of selecting a tomato plant exhibiting fruit with increased BRIX, comprising: a) crossing a tomato plant provided herein with itself or with a second tomato plant of a different genotype to produce one or more progeny plants; and b) selecting a progeny plant comprising said BRIX allele and lacking said deleterious allele. In some embodiments, selecting said progeny plant comprises detecting an S. *Lycopersicum* allele at M2 (SEQ ID NO:6) and detecting an *S. pennellii* allele at M3 (SEQ ID NO:11). In further embodiments, selecting said progeny plant further comprises detecting an *S. pennellii* allele at marker locus M9 (SEQ ID NO:41), and detecting an *S. lycopersicum* allele at marker locus M10 (SEQ ID NO:46). In certain embodiments, said progeny plant is an $F_2$-$F_6$ progeny plant. In further embodiments, producing said progeny plant comprises backcrossing.

BRIEF DESCRIPTION OF THE DRAWINGS

FIG. 1 shows the zone of necrosis measurement for a tomato plant. Necrosis is measured in the area 40 cm above and 40 cm below the last (youngest) fully ripened cluster of tomato fruit.

DETAILED DESCRIPTION

Fruit quality and taste are increasingly important traits in the production of food crops. Tomato consumers especially are interested in better tasting varieties. Many factors determine the flavor of a ripe tomato, but one predominantly used in the industry is the soluble solids content, or BRIX. BRIX levels in fruit are determined by environmental factors and genetics. Several alleles that increase BRIX levels have been identified in non-cultivated plant lines, however efforts to introduce these alleles into cultivated lines have been hindered by horticultural deficiencies. When a breeder introgresses a trait from a wild relative, observed horticultural deficiencies may be the result of either pleiotropy or linkage drag. Pleiotropy can typically overcome by several rounds of back crossing with the horticultural superior cultivated parent. However, overcoming linkage drag is significantly more difficult, and success is not assured.

Linkage drag is the result of unfavorable alleles tightly linked to the allele of interest. In some cases, it is possible that the unfavorable horticultural traits are even caused by the gene of interest. In addition, recombination is often suppressed in regions that are introgressed from wild relatives, especially if those relatives are further removed genetically. In the case of tightly linked linkage drag the development of markers and can help to assist the breeder in overcoming the unfavorably horticultural traits. In addition, recombination events can be developed to provide breeders with the smallest introgression of wild species DNA possible that can be used across breeding programs.

Efforts have been made to introgress alleles that increase the BRIX levels of tomato from uncultivated lines into cultivated tomato lines. For example, a locus that increases the BRIX levels of tomato fruit is located on chromosome 1 of the *Solanum pennellii* genome. The locus was found in a study of *S. pennellii* LA0716×*S. lycopersicum* cv. M82 introgression lines. These lines and derived sub-lines are available on request from the Hebrew University of Jerusalem or the Max Planck Institute of Molecular Plant Physiology (Alseekh, et al. 2013). In addition, LA0716 can be obtained from the Tomato Genetic Resource Centre in Davis, California, USA. However, these introgressions of the BRIX locus on chromosome 1 also carry a closely linked deleterious allele that causes necrosis of the leaves. This leaf necrosis is the most apparent in low-light conditions and is thus most readily found in tomato plants grown during the winter months. Leaf necrosis occurs often in tomato plants during a growth cycle, generally in the older lower leaves. This is can generally be tolerated by growers. However, the leaf necrosis caused by the allele closely linked to the BRIX increasing allele from *S. pennellii* on chromosome 1 occurs on the leaves around the ripening truss. This is an unacceptable trait for tomato growers and any variety exhibiting this type of necrosis is immediately considered unmarketable because of this. Obtaining fruit with increased BRIX content without unacceptable necrosis therefore remains a significant problem.

The present inventors have for the first time mapped both the BRIX increasing alleles and the linked deleterious necrosis alleles on chromosome 1, and developed a set of markers which can track the presence or absence of the BRIX alleles and the necrosis alleles during plant breeding. The inventors have further produced a reduced introgression comprising the BRIX increasing QTL on chromosome 1 that lacks the associated leaf necrosis linkage drag from *S. pennellii*. The BRIX QTL has been mapped to a 6.6 cM region between marker M3 (SEQ ID NO:11; a SNP change [A/G] at 96,871,421 bp), and marker M10 (SEQ ID NO:46; a SNP change [C/T] at 98,155,761 bp), while the leaf necrosis QTL is at about 1.2 cM distant from the BRIX locus at marker M1 (SEQ ID NO:1; a SNP change [G/C] at 96,680,481 bp), the proximal end of the BRIX QTL. To uncouple the two loci, the inventors have further developed novel molecular marker, M2 (SEQ ID NO:6; a SNP change [T/G] at 96,761,293 bp), that can be used to select for the increased BRIX QTL from *S. pennellii* and against the leaf necrosis QTL from *S. pennellii*.

The present inventors have discovered for the first time that the deleterious necrosis alleles can be removed from a plant containing a BRIX increasing introgression on chromosome 1 by selecting plants with a recombination event between marker loci M2 (SEQ ID NO:6) and M3 (SEQ ID NO:11), where marker locus M2 (SEQ ID NO:6) provides the *S. lycopersicum* allele and marker locus M3 (SEQ ID NO:11) the *S. pennellii* allele. In these plants the necrosis locus and BRIX increasing locus are uncoupled. In some embodiments, the size of *S. pennellii* introgression can vary at the distal end of the BRIX increasing QTL and can include the remainder of the distal arm of chromosome 1.

In further embodiments, in addition to a recombination event between marker loci M2 (SEQ ID NO: 6) and M3 (SEQ ID NO:11), a further recombination event between marker locus M9 (SEQ ID NO:41; a SNP change [A/G] at 97,237,436 bp), and marker locus M10 (SEQ ID NO:46) is detected. In this embodiment, an *S. pennellii* allele is present at marker locus M9 and an *S. lycopersicum* allele is present at M10. This version removes unwanted or unnecessary *S. pennellii* DNA at both the proximal and distal sides of the QTL resulting in introgression of the minimum amount of *S. pennellii* DNA needed to achieve an increased BRIX phenotype without leaf necrosis linkage drag.

In further embodiments, in addition to a recombination event between marker loci M2 (SEQ ID NO:6) and M4 (SEQ ID NO:16), a further recombination event between marker locus M12 (SEQ ID NO:56; a SNP change [G/A] at 97,062,157 bp), and marker locus M13 (SEQ ID NO:61; a SNP change [T/G] at 97,261,644 bp) is detected. In this embodiment, an *S. pennellii* allele is present at marker locus M12 and an *S. lycopersicum* allele is present at M13. This version removes unwanted or unnecessary *S. pennellii* DNA at both the proximal and distal sides of the QTL resulting in introgression of the minimum amount of *S. pennellii* DNA needed to achieve an increased BRIX phenotype without leaf necrosis linkage drag.

The invention further provides markers for tracking and identifying the novel recombinant introgressions in plants during breeding. A summary of useful markers is provided in Table 1. For example, marker loci M2 (SEQ ID NO:6), M3 (SEQ ID NO:11), M4 (SEQ ID NO:16; a SNP change [C/G] at 96,902,157 bp), M5 (SEQ ID NO:21; a SNP change [G/A] at 96,934,226 bp), M6 (SEQ ID NO:26; a SNP change [G/A] at 97,023,393 bp), M7 (SEQ ID NO:31; a SNP change [G/A] at 96,985,002 bp), M8 (SEQ ID NO:36; a SNP change [T/A] at 96,998,916 bp), M12 (SEQ ID NO:56), M9 (SEQ ID NO:41), M13 (SEQ ID NO:61), and M10 (SEQ ID NO:46). In certain embodiments, the BRIX locus may be selected for by detecting plants with an *S. pennellii* allele at one of M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M12 (SEQ ID NO:56), and/or M9 (SEQ ID NO:41). Plants without necrosis may then be detected by selecting in the previously selected plants for those plants with an *S. lycopersicum* allele at M2 (SEQ ID NO:6).

The invention further provides a breeding event comprising a reduced recombinant introgression from *S. pennellii* between marker loci M2 (SEQ ID NO:6) and M10 (SEQ ID NO: 46) which confers increased BRIX without necrosis. This breeding event may be used to introgress BRIX alleles from *S. pennellii* into any desired tomato genotype without deleterious linkage drag.

In certain embodiments, tomato plants are provided comprising an introgressed allele on chromosome 1, wherein said introgressed allele confers to the fruit of said plant increased BRIX compared to a plant not comprising said allele, wherein said plant lacks a further allele genetically linked to said introgressed allele, that confers necrosis when present.

In other embodiments, the invention provides plants comprising one or more of the novel recombinant introgressions provided herein. These novel introgressions provide fruit with increased BRIX, while avoiding the necrosis previously associated with BRIX-increasing alleles. Methods of producing the plants described herein are further provided.

Because genetically diverse plant lines can be difficult to cross, the introgression of BRIX-increasing alleles into cultivated lines using conventional breeding methods could require prohibitively large segregating populations for progeny screens with an uncertain outcome. Marker-assisted selection (MAS) is therefore essential for the effective introgression of BRIX alleles into elite cultivars without unacceptable necrosis. However, previously known markers for increased BRIX have failed to discriminate between donor DNA conferring a BRIX increase and donor DNA conferring deleterious traits. This has been further complicated by the previous inability to resolve the specific regions associated with increased BRIX. For the first time, the present invention enables effective MAS by providing improved and validated markers for detecting genotypes associated with increased BRIX and deleterious necrosis without the need to grow large populations of plants to maturity in order to observe the phenotype.

The invention therefore further provides novel trait-linked markers which can be used to produce plants comprising novel recombinant introgressions on chromosome 1 conferring increased BRIX levels as described herein. In particular embodiments, the invention provides the markers shown in Table 1. Other embodiments of the invention provide markers M1 (SEQ ID NO:1), M2 (SEQ ID NO:6), M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), M10 (SEQ ID NO:46), M11 (SEQ ID NO:51), M12 (SEQ ID NO:56), and M13 (SEQ ID NO:61) on chromosome 1, which can be used to track BRIX and necrosis alleles in tomato plants during breeding.

Methods of producing plants comprising the reduced recombinant introgressions described herein are further provided. In some examples, donor DNA from a high BRIX donor parent is introgressed into a cultivated plant line (the recurrent parent line). In certain embodiments, plants can be selected based on detection of recurrent parent DNA at marker loci M2 (SEQ ID NO:6) and M13 (SEQ ID NO:61) or M10 (SEQ ID NO:46) and donor DNA at a marker locus selected from the group consisting of M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M12 (SEQ ID NO:56), and M9 (SEQ ID NO:41).

In certain embodiments, the invention provides methods of producing or selecting a tomato plant exhibiting fruit with increased BRIX without necrosis comprising: a) crossing a tomato plant provided herein with itself or with a second tomato plant of a different genotype to produce one or more progeny plants; and b) selecting a progeny plant comprising a BRIX allele and lacking a necrosis allele. In some embodiments, methods of the invention comprise selecting a progeny plant by detecting at least one polymorphism at a locus selected from the group consisting of marker locus M2 (SEQ ID NO:6), M3 (SEQ ID NO:11), M4 (SEQ ID NO:16), M5 (SEQ ID NO:21), M6 (SEQ ID NO:26), M7 (SEQ ID NO:31), M8 (SEQ ID NO:36), M9 (SEQ ID NO:41), M10 (SEQ ID NO:46), M12 (SEQ ID NO:56), and M13 (SEQ ID NO:61).

I. Genomic Regions, Alleles, and Polymorphisms Associated with BRIX and Necrosis in Tomato Plants The invention provides novel introgressions of one or more alleles associated with increased BRIX without detrimental necrosis in tomato plants, together with polymorphic nucleic acids and linked markers for tracking the introgressions during plant breeding.

Tomato lines exhibiting BRIX are known in the art and may be used together with the novel trait-linked markers provided herein in accordance with certain embodiments of the invention. For example, the wild tomato accession *Solanum pennellii* LA0716 (available from the Tomato Genetic Resource Center in Davis, CA, USA), can be used as a source for BRIX-increasing alleles. Using the improved genetic markers and assays of the invention, Applicants were able to successfully identify novel reduced introgression from *S. pennellii* that confer increased BRIX to the fruit of a plant with fewer deleterious traits when introgressed into a cultivated line. In certain embodiments, the invention provides tomato plants comprising donor DNA between marker locus M3 (SEQ ID NO:11) and M10 (SEQ ID NO:46) on chromosome 1.

The novel introgressions provided herein confer robust increases in BRIX, while avoiding the necrosis seen with conventional introgressions. The invention therefore represents a significant advance in the art.

II. Introgression of Genomic Regions Associated with Increased BRIX

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a donor plant comprising BRIX-increasing alleles into a cultivated line. The invention further provides markers for identifying and tracking the novel introgressions disclosed herein during plant breeding, including the markers set forth in Table 1.

Markers within or linked to any of the genomic intervals of the present invention may be useful in a variety of breeding efforts that include introgression of genomic regions associated with increased BRIX into a desired genetic background. For example, a marker within 40 cM, 20 cM, 15 cM, 10 cM, 5 cM, 2 cM, or 1 cM of a marker associated with increased BRIX levels described herein can be used for marker-assisted introgression of genomic regions associated with a disease resistant phenotype.

Tomato plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Tomato plants comprising an introgressed region comprising regions closely linked to or adjacent to the genomic regions and markers provided herein and associated with an increased BRIX phenotype are also provided.

III. Development of Tomato Varieties with Increased BRIX

For most breeding objectives, commercial breeders work within germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated tomato types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and negative linkage drag from the non-cultivated parent. For example, non-cultivated tomato types can provide alleles associated with increased fruit quality. However, these non-cultivated types may have poor horticultural qualities such as increased necrosis.

The process of introgressing desirable genes from non-cultivated lines into elite cultivated lines while avoiding problems with linkage drag or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as increased fruit quality. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with increased BRIX disclosed herein can be introgressed from one genotype to another and tracked using MAS. Thus, the inventors' discovery of accurate markers associated with increased BRIX will facilitate the development of tomato plants having beneficial phenotypes. For example, seed can be genotyped using the markers of the present invention to select for plants comprising desired genomic regions associated with increased BRIX. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rina gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Marker Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) Genomics, 8(2), 271-278), denaturing gradient gel electrophoresis (Myers (1985) EPO 0273085), or cleavage fragment length polymorphisms (Life Technologies, Inc., Gathersberg, MD), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) Biotechniques 12(1), 82-87), or PCR amplification of multiple specific alleles (PAMSA; Dutton and Sommer (1991) Biotechniques, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with increased BRIX levels, identify a tomato plant with a genotype associated with increased BRIX levels, and to select a tomato plant with a genotype associated with increased BRIX levels. In certain embodiments of methods of the invention, polymorphic nucleic acids can be used to produce a tomato plant that comprises in its genome an introgressed locus associated with increased BRIX levels. In certain embodiments of the invention, polymorphic nucleic acids can be used to breed progeny tomato plants comprising a locus or loci associated with increased BRIX levels.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with increased BRIX levels in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1. Measuring BRIX and Determining Necrosis Levels

BRIX, or soluble solids content, is measured routinely in the tomato industry and is often used as a proxy for flavor. For the BRIX measurement, a BRIX meter is used, which is a digital refractometer calibrated using a series of sucrose solutions. While the method of measuring BRIX in a sample is standard across the industry, the harvest method to produce the sample is not. All harvest methods will work if samples are harvested and processed at the same time, and fruit samples are picked consistently across all plants. This is very important because the BRIX level is heavily influenced by environmental conditions and fruit ripeness. For example, fruit harvested at a different time in the year from the same plant can have significantly different levels of BRIX. Therefore, BRIX is often expressed as a relative value compared to a control. What the control is depends on the experiment, but can be for example a recurrent parent, a sister line without the introgression of interest, or a standard variety. The following harvesting method was used in the examples described herein. All plants were harvested twice (H1 and H2). The H1 harvest is when the second truss of the last entry has reached 80% maturity. This means that 80% of the fruit of the truss have fully turned to the mature fruit color. For each plant the latest truss that reached 80% or more ripe fruit is harvested. Generally, the 2 fruit at the base of the truss are taken (closest to the stem). For smaller fruited types this can be the 4 or 6 fruits closest to the stem of the plant. The H2 harvest is at the end of the experiment where the same harvest protocol is used as for the H1 harvest. Fruit of a single plant are pooled and homogenized. The BRIX content is then determined for the homogenized sample.

Necrosis is determined in adult plants with normal fruit load. The leaf necrosis is best observed in an environment with no artificial light, as this can cause its own form of leaf necrosis, and under generally lower light conditions, as typically observed during the winter months. Plants should be sown such that the adult plants are in the experimental low light conditions from early autumn (mid-September or October) to April. Plants are grown using methods commonly used by tomato growers. Scoring of leaf necrosis starts when the positive control plants show leaf necrosis of an intermediate level, which corresponds to clear and/or intense necrosis spots on <10% of the leaf surface. Other categories for scoring can include (with increasing severity): no symptoms, minor necrosis symptoms on the leaf edge, clear necrosis symptoms on the leaf edge, minor necrosis spots on <10% of the leaf surface, clear necrosis spots on <10% of the leaf surface, intense necrosis spots on <10% of the leaf surface, necrosis on <20% of the leaf surface, necrosis on <50% of the leaf surface, and necrosis on >50% of the leaf surface. This should not be before a plant has produced two fully ripe fruit clusters. The level of necrosis is scored for the leaves in a zone extending about 40 cm above and about 40 cm below the truss that is ripening at that time (FIG. 1). This zone is a relative location and the exact distance from the ground can vary due to variation in fruit setting and growth rates between the tested plants. It is important that the experiment contains adequate positive and negative control plants. Positive control plants are for example the inbred line IL1-4 obtainable from Zamir or Fernie (Alsheekh, et al. 2013) or plants with *S. pennellii* alleles at marker M1 (SEQ ID NO:1) and M2 (SEQ ID NO:6). A good negative control is the parent line with the *S. pennellii* introgression on chromosome 1. While the intensity of necrosis varies depending on the genetic background, the necrosis can be observed in all cases.

Example 2. Removing Deleterious Traits on Chromosome 1

Previous research has identified several loci, including pen1 (derived from *S. pennellii* line LA0716), with potential to increase flavor by increasing BRIX (soluble solids content in aqueous solution (g/100 mL)). It was found that the original introgressions of this BRIX locus showed a significant increase in BRIX level, but also showed the undesirable trait of leaf necrosis. To ensure minimal (or no) introgression of associated detrimental traits, experiments were conducted to create recombinants around the pen1 locus and evaluate these recombinants for both BRIX levels and necrosis severity. A series of markers was developed to map the leaf necrosis and BRIX alleles (Table 1). The original interval was 18.1 cM wide and was narrowed down to a 4 cM region by evaluating a set of recombinants from a BC1F4 cross between the determinate source LEASE carrying the *S. pennellii* segment and the indeterminate breeding line FIR-150-2044. After evaluation, it became clear that this original reduced segment still contained the leaf necrosis. To map the location of the necrosis and BRIX QTLs, an additional set of SNP markers was developed. In a subsequent mapping using a BC1F5 population from the FIR-150-2044×LEASE cross, it was possible to map the leaf necrosis phenotype (at marker loci M1 and M2) at 0.9 cM distance from the BRIX increasing allele, starting at marker locus M4 (SEQ ID NO:16).

To validate the removal of the deleterious necrosis trait on chromosome 1, a second population was developed with a recurrent parent that was much more sensitive to leaf necrosis than the recurrent parent used in the original mapping. This experiment was run in the winter period to ensure optimal conditions for the appearance of leaf necrosis. Sister lines with and without *S. pennellii* introgressions were coupled in the experiment and placed randomly within replications. The plants were phenotyped as previously described and genotyped using the same markers as for the initial mapping population. The results from this experiment confirmed that a recombination event between marker M2 and markers M3 or M4 would remove the deleterious necrosis trait from the BRIX increasing locus.

TABLE 1

List of markers and favorable alleles at each marker for breeding event creation.

| Marker name | Fav allele | Chr. | Genetic Position (cM) | Public position marker (bp) (SL3.0) | Public position SNP (bp) (SL3.0) | Marker size (bp) | SNP position in marker (bp) | SNP change | Fav Allele | Marker sequence | Fwd primer | Rev primer | Probe 1 | Probe 2 |
|---|---|---|---|---|---|---|---|---|---|---|---|---|---|---|
| M1 | rp | 1 | 154.5 | 96,680,541-96,680,422 | 96,680,481 | 123 | 61 | G/C | G | 1 | 2 | 3 | 4 | 5 |
| M2 | rp | 1 | 155 | 96,760,850-96,761,549 | 96,761,293 | 700 | 443 | T/G | T | 6 | 7 | 8 | 9 | 10 |
| M3 | donor | 1 | 155.7 | 96,871,011-96,872,011 | 96,871,421 | 1001 | 411 | A/G | G | 11 | 12 | 13 | 14 | 15 |
| M4 | donor | 1 | 155.9 | 96,901,574-96,902,518 | 96,902,157 | 972 | 611 | C/G | G | 16 | 17 | 18 | 19 | 20 |
| M5 | donor | 1 | 156.1 | 96,933,578-96,934,569 | 96,934,226 | 995 | 651 | G/A | A | 21 | 22 | 23 | 24 | 25 |
| M6 | donor | 1 | 156.3 | 97,023,453-97,023,334 | 97,023,393 | 121 | 61 | G/A | G | 26 | 27 | 28 | 29 | 30 |
| M7 | donor | 1 | 156.4 | 96,984,621-96,985,457 | 96,985,002 | 843 | 382 | G/A | G | 31 | 32 | 33 | 34 | 35 |
| M8 | donor | 1 | 156.5 | 96,998,808-96,999,921 | 96,998,916 | 1114 | 108 | T/A | A | 36 | 37 | 38 | 39 | 40 |
| M12 | donor | 1 | 156.9 | 97,061,857-97,062,457 | 97,062,157 | 601 | 301 | G/A | G | 56 | 57 | 58 | 59 | 60 |
| M9 | donor | 1 | 158 | 97,236,955-97,237,935 | 97,237,436 | 980 | 481 | A/G | G | 41 | 42 | 43 | 44 | 45 |
| M13 | rp | 1 | 158.2 | 97,261,344-97,261,944 | 97,261,644 | 601 | 301 | T/G | G | 61 | 62 | 63 | 64 | 65 |
| M10 | rp | 1 | 161.6 | 98,155,701-98,155,818 | 98,155,761 | 121 | 61 | C/T | C | 46 | 47 | 48 | 49 | 50 |
| M11 | rp | 1 | 164.3 | 97,847,339-97,845,480 | 97,845,746 | 1877 | 1592 | A/G |  | 51 | 52 | 53 | 54 | 55 |

"rp" = recurrent parent allele
"donor" = donor allele

Example 3. Validation of the BRIX Increasing Locus

To ensure that the BRIX increasing locus on chromosome 1 would be efficacious across different genotypic backgrounds, populations of three different tomato types, large medium tomato type ($BC_3F_2$ population, 96 plants), pink tomato type ($F_2$ population, 101 plants) and the cherry tomato type ($BC_2F_4$ population, 98 plants), segregating for the BRIX allele on chromosome 1 were tested for efficacy of the BRIX allele. The populations were randomly planted in a greenhouse and each plant was evaluated for genotype and BRIX. In each population three classes of genotypes were found: heterozygous, homozygous for the presence of the BRIX allele, and homozygous for the absence of the BRIX allele. The data was then analyzed for each population independently and it was found that the BRIX increasing locus on chromosome 1 had a significant effect on BRIX increase in all three of the populations (Table 2).

TABLE 2

Statistical analysis of three different tomato type populations for the effect of the BRIX QTL on chromosome 1.

| Population | $R^2$ QTL effect | P-value | Mean BRIX value −/− | +/− | +/+ |
|---|---|---|---|---|---|
| Large medium | 0.27 | <0.0001 | 4.84 | 5.20 | 5.46 |
| Pink | 0.10 | 0.0088 | 6.74 | 7.24 | 7.42 |
| Cherry | 0.11 | 0.0042 | 8.22 | 8.66 | 8.69 |

Example 4. Breeding Event Creation

To aid breeding efforts, a breeding event donor was developed for the BRIX increasing allele without the detrimental necrosis allele that could be used across different breeding programs. The first step in creating this event donor was selecting plants with a recombination event between M2 (SEQ ID NO:6) and M3 (SEQ ID NO:11) from the fine-mapping population. The plants were then used to develop $BC_4F_2$ material. These plants were then evaluated and compared to the *S. lycopersicum* parent (FIR-150-244, plants with no necrosis and no BRIX increase) and the $BC_1F_4$ plants that contained the full interval (plants with necrosis and BRIX increase) in a randomized block design with 5 replications and 4 plants per plot. Here it was found that all four tested lines with a recombination event between M2 (SEQ ID NO:6) and M3 (SEQ ID NO:11) showed increased BRIX (Table 3) and absence of necrosis (Table 4). These lines could be used as event donors, but one could also choose to shorten the amount of *S. pennellii* DNA at the other side of the BRIX allele. To do this one can look for a recombination event between M5 (SEQ ID NO:21) and any marker southwards, or between two markers south of M5. For example, between M9 (SEQ ID NO:41) and M10 (SEQ ID NO:46), which is what was chosen for the breeding event described here. Table 1 provides an overview of markers and their preferred alleles for the development of the breeding event described here. Further shortening of the breeding event while maintaining increased BRIX is possible by selecting for plants with a recombination event between M12 (SEQ ID NO:56) and M13 (SEQ ID NO:61). In this case, one selects for the *S. pennellii* donor allele at M12 and the *S. lycopersicum* recurrent parent allele at M13.

TABLE 3

Statistical analysis of BRIX measures for breeding event lines compared to the recurrent parent (no BRIX increase) and the BC1F4 plants with a full interval (BRIX increase) for two harvests. Those materials not statistically different from each other are placed in the same group.

| Material | Brix | | | |
|---|---|---|---|---|
| | Group | LSM H1 | Group | LSM H2 |
| Full interval | A | 3.9 | B | 4.8 |
| Breeding event | A | 3.7 | A | 5.2 |
| FIR-150-2044 | B | 3.3 | C | 4.3 |

TABLE 4

Statistical analysis of leaf necrosis measures for breeding event lines compared to the recurrent parent (no BRIX increase) and the BC1F4 plants with a full interval (BRIX increase). Those materials not statistically different from each other are placed in the same group.

| Material | Necrosis | |
|---|---|---|
| | Group | LSM |
| Check_full interval | A | 2.9 |
| Breeding event | B | 1.7 |
| RP FIR-150-2044 | B | 2.0 |

---

What is claimed is:

1. A *Solanum lycopersicum* plant comprising a recombinant chromosomal segment on chromosome 1, wherein said chromosomal segment comprises an introgressed BRIX allele found in *S. pennellii* line LA0716 conferring increased BRIX to the fruit of said plant compared to the fruit of a plant not comprising said allele, wherein said chromosomal segment lacks a deleterious allele genetically linked to said BRIX allele that confers necrosis to said plant when present, and wherein said chromosomal segment is found in *S. pennellii* line LA0716 and is flanked by marker locus M3 having SEQ ID NO:11 or marker locus M4 having SEQ ID NO:16 and a marker locus selected from the group consisting of marker locus M5 having SEQ ID NO:21, marker locus M6 having SEQ ID NO:26, marker locus M7 having SEQ ID NO:31, marker locus M8 having SEQ ID NO:36, marker locus M9 having SEQ ID NO:41, and marker locus M12 having SEQ ID NO:56.

2. The plant of claim 1, wherein said BRIX allele is located within a chromosomal segment in the genome of said plant between positions 96,871,421 bp and 96,934,226 bp on the Tomato SL3.0 map.

3. A plant part of the plant of claim 1, wherein said plant part comprises the recombinant chromosomal segment on chromosome 1.

* * * * *

SEQUENCE LISTING

```
<160> NUMBER OF SEQ ID NOS: 65

<210> SEQ ID NO 1
<211> LENGTH: 121
<212> TYPE: DNA
<213> ORGANISM: Solanum pennellii
<220> FEATURE:
<221> NAME/KEY: misc_feature
<222> LOCATION: (99)..(99)
<223> OTHER INFORMATION: n is a, c, g, or t

<400> SEQUENCE: 1
acagagctaa gaattacttg tggctggtga accagcagaa gctttccaat taaaatgttg      60 sccttttccag tcggttattg ttcctccagc accttctant actggtacaa gtgagaggaa    120
g                                                                     121

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
gaaccagcag aagctttcca attaa                                            25

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
aggtgctgga ggaacaataa cc                                               22

<210> SEQ ID NO 4
<211> LENGTH: 17
<212> TYPE: DNA
<213> ORGANISM: Artificial Sequence
<220> FEATURE:
<223> OTHER INFORMATION: Probe

<400> SEQUENCE: 4
actggaaagg gcaacat                                                     17

<210> SEQ ID NO 5
<211> LENGTH: 17
<212> TYPE: DNA
```

```
<213> ORGANISM: Artificial Sequence
<220> FEATURE:
<223> OTHER INFORMATION: Probe

<400> SEQUENCE: 5
actggaaagg ccaacat                                                     17

<210> SEQ ID NO 6
<211> LENGTH: 700
<212> TYPE: DNA
<213> ORGANISM: Solanum pennellii
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t

<400> SEQUENCE: 6
tctttgccca cttacaggat gaaatcgaat acaaagctgt gaagagactc cataaatcac       60
cctaatgcaa aggcctctag aaatatccca tactctgaca gttttatcca ttgaagatga      120
tgcaatgtac tgattgtttg tggagaagtc aaaatctgaa aaaaggtcag atttcaaaaa      180
taataacagt aacatgttaa acatagataa agcatagcta gcatttagtc cctcttgacc      240
gaggaacaga cttgcaatta gagtcacaaa gaggcatgnt aagaaaatca aaaggaactc      300
cataagagca ccatagtgtg gtttctggct ttctggatta ctcagtttag accntcaatg      360
gattggggta ggaactaaaa cacatgaact aatttcgcat atccagaaaa ctatgagaat      420
taaaaggatt ctttacaaaa cckatatcaa atttgaaata agaggtttaa ataaagtact      480
aacattaaaa gactcgtgtg atgataaaag ctcttggaaa agccgggtat caaaagaaag      540
tgctgccttt ctgtcaactc aaaatgaggc ttaacaacaa ccaccaatat ttgagtttgg      600
ancaaaacta atanaaaatt aataaaaaga agaaantaat tttttttgtaa ggtaataaaa      660 ttgctgtttt agtgggtcat atatacatgg ggagggtgtt                            700

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
cacatgaact aatttcgcat atccagaaa                                        29

<210> SEQ ID NO 8
<211> LENGTH: 35
<212> TYPE: DNA
<213> ORGANISM: Artificial Sequence
<220> FEATURE:
<223> OTHER INFORMATION: Primer
```

```
-continued

<400> SEQUENCE: 8
tcatcacacg agtcttttaa tgttagtact ttatt                              35

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
ctttacaaaa ccgatatcaa                                              20

<210> SEQ ID NO 10
<211> LENGTH: 22
<212> TYPE: DNA
<213> ORGANISM: Artificial Sequence
<220> FEATURE:
<223> OTHER INFORMATION: Probe

<400> SEQUENCE: 10
ttctttacaa aacctatatc aa                                           22

<210> SEQ ID NO 11
<211> LENGTH: 1001
<212> TYPE: DNA
<213> ORGANISM: Solanum pennellii
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (487)..(488)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
```

```
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t

<400> SEQUENCE: 11
aagggacaac agtcaaactt gactaataaa taataatcac tacccattca aggaaacaca      60
acaaagccat tccagctaaa atcctcaatt acttgttagc tttataatgt catngttgtc     120
ttcagaagac ctctcaaaca tactgagaaa cagcaatagt aacttctcaa aaacttgtgt     180
tcnaactcga taacttgaat accaaaacat taaaaccttc agctgaccaa aaaactgatg     240
nttaatgctg gatgaggggt ttnaactcac gataacttat gtgaacaaga taagcagaat     300
ttcagattaa acaaagaaat gtagcagagt gaacatcntt atccactaac caaggtgaat     360
attgtatgac tgcggctact aaacagattg aaattatttg aaccaacgtg rcggtgctct     420
gcaacattaa gaatgtaatc aanatcagga tccacgaaag cttgcctata tantcagcag     480
gatccannaa agcttgccta tgaaaaaatg tgacttccgg acaagaaaca gattcaannaa    540 ttaccttccc cagcagcaat aaacgaaaga gcatgcccag gtgacaaaac aacttcctcc     600
ttcataccct caacataagt accctgcata atagcaagta taaaanaatg acgaaccata     660
nagcagcatt acaatcatga actatgatag aaaaacatna anatctattt tctagtagaa     720
caactacagg ctaaaagcac cacctgcagt gctggnaggt aatgataggt tttgatcttc     780
aggtgacaaa aagaagcta natttttgttt atttcttagt acatctcagn aantaaaatag    840 gnattantan gtttgnttat atttttcctg ataaatnaag actcgggcat gtgataacat     900
```

```
gtaggaaaca cttttcctta tcttattatt tacaaaatat actaaaatgg ttgtcctagc    960 cataggaac acagctattc tttgattctt ctcataaaaa c                        1001
```

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12

```
actgcggcta ctaaacagat tgaaa                                         25
```

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13

```
gcaagctttc gtggatcctg at                                            22
```

<210> SEQ ID NO 14
<211> LENGTH: 15
<212> TYPE: DNA
<213> ORGANISM: Artificial Sequence
<220> FEATURE:
<223> OTHER INFORMATION: Probe

<400> SEQUENCE: 14

```
ccaacgtggc ggtgc                                                    15
```

<210> SEQ ID NO 15
<211> LENGTH: 15
<212> TYPE: DNA
<213> ORGANISM: Artificial Sequence
<220> FEATURE:
<223> OTHER INFORMATION: Probe

<400> SEQUENCE: 15

```
ccaacgtgac ggtgc                                                    15
```

<210> SEQ ID NO 16
<211> LENGTH: 972
<212> TYPE: DNA
<213> ORGANISM: Solanum pennellii
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (90)..(91)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:

-continued

```
<221> NAME/KEY: misc_feature
<222> LOCATION: (107)..(112)
<223> OTHER INFORMATION: n is a, c, g, or t
<220> FEATURE:
<221> NAME/KEY: misc_feature
<222> LOCATION: (117)..(119)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (128)..(130)
<223> OTHER INFORMATION: n is a, c, g, or t
<220> FEATURE:
<221> NAME/KEY: misc_feature
<222> LOCATION: (132)..(136)
<223> OTHER INFORMATION: n is a, c, g, or t
<220> FEATURE:
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (353)..(360)
<223> OTHER INFORMATION: n is a, c, g, or t
<220> FEATURE:
<221> NAME/KEY: misc_feature
<222> LOCATION: (362)..(364)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
```

```
<220> FEATURE:
<221> NAME/KEY: misc_feature
<222> LOCATION: (466)..(467)
<223> OTHER INFORMATION: n is a, c, g, or t
<220> FEATURE:
<221> NAME/KEY: misc_feature
<222> LOCATION: (511)..(511)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (928)..(928)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t

<400> SEQUENCE: 16
cttatctatc aactttcaaa tttaagagac aagtgcgtta tntttcactt tattttggtt      60
cgatcccaat cttattaaag ggaaaataan ntttnnttan attnnannnn nncaatnnnt     120
gtnntctnnn cnnnnnannt ntctttngtg atttngactt gaantttttt taagantnaa     180
tattgaaatc cgtctacttc atcacnttct ttccttttca aaatgaataa aatttgactt     240
acataatatc ttcataaatt antcaccaaa atagatagct cttttaaata aatttatgaa     300
aaacaaaata tataaactta ctataataaa tttgttttt gnaattaata tannnnnnnn     360
annntntata atctagacat tgtcttcctc ttttttattg cagtattatc ctgccttta     420 tgttagtaan tgtgactgcc tctttcattt atctgttcaa atntgnntca cttttttcata     480 tataaagaa acaaccaaac agtttttttt nttcaaaatn acttcaattt tatcaattgt     540
acctccatgg ctnctnttcg taagagnttg ttgaacccgg atgcatccga atatatacct     600
atttccactc sgccaccncc tcctcctcct cctaccgttg attcaccacc acgggagaat     660
gtgcgatcgc catcggtgga acacccgtgg ttgaacattc ctcctagatt gatnaatgat     720
tatgtctcta gaacaaaatt ttctccatcc attaagggaa tcagaggtga agagtggtcg     780
aaaaacgatg gcccgacgaa atacagatac agtgttatac ctataagaag gagccataag     840
aacgtgacta ctatcgtgat taagaatatt ccatatgact acaagtaatt ttaatctatt     900
taattgttca gattactttt tctgggangn tgattataac aaaatttaat ggtttgactc     960
tctagtggca ta                                                        972

<210> SEQ ID NO 17
```

```
<211> LENGTH: 25
<212> TYPE: DNA
<213> ORGANISM: Artificial Sequence
<220> FEATURE:
<223> OTHER INFORMATION: Primer

<400> SEQUENCE: 17
aacccggatg catccgaata tatac                                         25

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ggtggtgaat caacggtagg a                                             21

<210> SEQ ID NO 19
<211> LENGTH: 19
<212> TYPE: DNA
<213> ORGANISM: Artificial Sequence
<220> FEATURE:
<223> OTHER INFORMATION: Probe

<400> SEQUENCE: 19
ctatttccac tccgccacc                                                19

<210> SEQ ID NO 20
<211> LENGTH: 16
<212> TYPE: DNA
<213> ORGANISM: Artificial Sequence
<220> FEATURE:
<223> OTHER INFORMATION: Probe

<400> SEQUENCE: 20
tttccactcg gccacc                                                   16

<210> SEQ ID NO 21
<211> LENGTH: 995
<212> TYPE: DNA
<213> ORGANISM: Solanum pennellii
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
```

```
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t

<400> SEQUENCE: 21
ttgttttaaa tttnnttttt gaacttccat tgaacgttgc aggtatgcat attctatttg      60
gtccttcgag cacttgacac tgttggtaag ctcagttact atcatctaaa tttgcttgta     120
ctttatgaat gcttaggaga tatgaaactc agaaagtatt anttcttcat tttttgtgca     180
aaatttggtg taattaattt antcttctat ctttgaaaga gtaggttgaa tcgttgattt     240
agttcatcat gcttatcttc tattncntct tgagaggaac aaaagatgac gagagaggga     300
ataataactt gttgaaaatt tcaactgctt attaattaaa aagaggaaaa gatgcaagct     360
gttcttcctt atcnaaaaaa aaaaaggaaa agaagcaagt cgttcttctc atactagtta     420
tattggtatt tgatatttag cttatatgat actgngctgc ctaccagctt cctgttgaac     480
tcttcttggt tataaacaag ttctgacnaa cttttnttgc ttaaatacta gtaggaatta     540
tcatatgcta cttattattt catttcattc tagacattca caaggtagtt tttaggttgt     600
aatcttagct gattcaaggg ttgttgcagt catattttg agtaacacat rttttgctta      660
tttttcatat ttggntgttc ttattgtgga cagaggatga taccagcata cccaccgatg     720
ttaaagtacc natnttgatc tcttttcatc agcatgttta tgatcgcgaa tggcactttg     780
catgtaagtc tctgaatgca acttgttgat ctccctaagt tctcaatatt gcttctctct     840
tattannagn gtacttttgc aattgaagaa tcccaagttg gaatgacttc aactactttt     900
tagaggttac taaggagatt attttgaata agtcagatgg aaaccaatnc aaaatatttc     960
actgtctacc caaaaatgtt tttcttttgc tgcac                                995

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
```

```
tgattcaagg gttgttgcag tcata                                              25
```

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23

```
ctggtatcat cctctgtcca caat                                               24
```

<210> SEQ ID NO 24
<211> LENGTH: 20
<212> TYPE: DNA
<213> ORGANISM: Artificial Sequence
<220> FEATURE:
<223> OTHER INFORMATION: Probe

<400> SEQUENCE: 24

```
ttgagtaaca catgttttgc                                                    20
```

<210> SEQ ID NO 25
<211> LENGTH: 19
<212> TYPE: DNA
<213> ORGANISM: Artificial Sequence
<220> FEATURE:
<223> OTHER INFORMATION: Probe

<400> SEQUENCE: 25

```
tgagtaacac atattttgc                                                     19
```

<210> SEQ ID NO 26
<211> LENGTH: 121
<212> TYPE: DNA
<213> ORGANISM: Solanum pennellii
<220> FEATURE:
<221> NAME/KEY: misc_feature
<222> LOCATION: (31)..(31)
<223> OTHER INFORMATION: n is a, c, g, or t

<400> SEQUENCE: 26

```
aagatgtgaa agatttcaac agaacttatg ncggctataa tttcaaggct tcttgttgat        60
rgctgagaaa tccctgcttg ccagtagtga cattttgaaa ttcagtggaa aatgggctcc       120
a                                                                       121
```

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27

```
aagatgtgaa agatttcaac agaacttatg                                         30
```

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28

```
tcaaaatgtc actactggca agca                                               24
```

<210> SEQ ID NO 29
<211> LENGTH: 20
<212> TYPE: DNA
<213> ORGANISM: Artificial Sequence
<220> FEATURE:
<223> OTHER INFORMATION: Probe

<400> SEQUENCE: 29
atttctcagc tatcaacaag                                               20

<210> SEQ ID NO 30
<211> LENGTH: 16
<212> TYPE: DNA
<213> ORGANISM: Artificial Sequence
<220> FEATURE:
<223> OTHER INFORMATION: Probe

<400> SEQUENCE: 30
ctcagccatc aacaag                                                   16

<210> SEQ ID NO 31
<211> LENGTH: 843
<212> TYPE: DNA
<213> ORGANISM: Solanum pennellii
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:

-continued

```
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (638)..(639)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (670)..(672)
<223> OTHER INFORMATION: n is a, c, g, or t
<220> FEATURE:
<221> NAME/KEY: misc_feature
<222> LOCATION: (674)..(675)
<223> OTHER INFORMATION: n is a, c, g, or t
<220> FEATURE:
<221> NAME/KEY: misc_feature
<222> LOCATION: (696)..(697)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (757)..(759)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
```

```
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t

<400> SEQUENCE: 31
cacacaccta ctagtaatag tagnnagaag agaagaagct tagaaaaaaa aatgaagana      60
aanatnattt cttcaaaatt aatgctgctt cttctccttc ttcttccatt attaaactgc     120
catggaagct accttgatta tacagangca ttnaccaaat ccattctctt cttcgaaggc     180
caacgctccg gctatttacc gcaggaccag agaatganct ggcgaggaca ttccggttta     240
agcgatggat gggagatgaa tgttgatttg accggcggtt actacgacgc cggagataat     300
gtgaagttta attttccgat ggcgtttacg acgacgttgc ttgcgtggag tgtaattgaa     360
tttggggaaa ttatgccgcc trctgaatta cggaatgntt tagtcgctat ccgttggtcc     420
actgattatc ttctcaaaac tgtttctcag ccagatcgca ttttcgtcca ggtttgttat     480
tcactttttt anttattatt ttttggatgg gactaaacga acaaaattaa naacaacatc     540
aacaacagna atcccgcaa gtgnaatata ganagggtaa aancgtatat ttaatcntat      600
cactttttng cagagatana aanantgttt ccgcnaanna accaactntt ttatgctctg     660
tttctactgn nntnngtatg ttttgtgcat gtaaanntat tactcctctg tttttacatt     720
ttgtgattat aagnatgtca ttnatnaatt aagaggnnnt aatgnttttt ttaagaaaaa     780
attagccaaa atattttaga aatacgaaat tgntattatn ttttnanaaa agattaatag     840
tgg                                                                  843

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
ttgcgtggag tgtaattgaa tttgg                                            25

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
ggaccaacgg atagcgacta aa                                               22

<210> SEQ ID NO 34
<211> LENGTH: 17
<212> TYPE: DNA
<213> ORGANISM: Artificial Sequence
<220> FEATURE:
<223> OTHER INFORMATION: Probe

<400> SEQUENCE: 34
tatgccgcct gctgaat                                                     17

<210> SEQ ID NO 35
```

```
<211> LENGTH: 17
<212> TYPE: DNA
<213> ORGANISM: Artificial Sequence
<220> FEATURE:
<223> OTHER INFORMATION: Probe

<400> SEQUENCE: 35
tatgccgcct actgaat                                                    17

<210> SEQ ID NO 36
<211> LENGTH: 1095
<212> TYPE: DNA
<213> ORGANISM: Solanum pennellii
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (698)..(699)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
```

<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t

<400> SEQUENCE: 36

```
gcntaccgta ccttgctggt gtcagctcca ggccttggac agtacatctc tggtgctatt      60
cttttttgagg agaccctcta ccagtctacc gtngatggac gcaaaatwgt tgatgttctt    120
attgagcaaa acattgttcc tggtatcaaa gttgacaagg tatattaacc tgcacccaca    180
acttgaaaaa ggacaatagt aaagagttat tgttgctggt gnaaaaatat agcgaacttt    240
tattttgtat aatattggtc tgagcagaaa cttaaatgga atgacatgat cagtnaggat    300
ttgtataacc gaccccaact tgcttggtca tatatgtggt tatactaacn atagaagagg    360
aaaggcaggn ttntaactgt ttancaagaa caagttatac tgaaatgaga tttctgtcaa    420
tctcctaatc attatatctg ttcacagggt ttggttcccc ttgctggttc aaatgatgan    480
tcatggtgtc aaggtcttga tggacttgcc tcgcgctctg ctgcatacta ccaacaggga    540
gcacgtttcg ccaaatggta catttggagt cctaattcac tttgttattt tctcataatg    600
cacancggaa gaagaaaaaa tttatatgga cnataccaaa tagttgtttn aaanggtctt    660
tttcatcatg ttagaagttt atatgctaat ctatcctnnt tttgcacaat attggtantg    720
agatgaatta aantagagcg acaagtcagt gaagattcat atacccgacc catgttaaga    780
ttaatgctaa aattatggta actnataggc gtaccgtggt gagcattccc aacggaccat    840
ctgcattggc tgtnaaggaa gcagcatggg gcttggctcg ctacgctgcc atttctcagg    900
acaatggttt ggtcccaatt gtggagccag agatcttgtt ggacggtgaa cacggcattg    960
acaggacttt tgaggtagca cagaaggtct gggctgaagt cttcttctac ttggctgaga   1020
acaatgtcat gtttgagggt atcctcttga aaccnagcat ggttactcct ggtgctgaat   1080
gcaaagacag ggcca                                                    1095
```

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37

```
gaggagaccc tctaccagtc tac                                              23
```

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38

```
gataccagga acaatgtttt gctcaa                                           26
```

<210> SEQ ID NO 39

```
<211> LENGTH: 16
<212> TYPE: DNA
<213> ORGANISM: Artificial Sequence
<220> FEATURE:
<223> OTHER INFORMATION: Probe

<400> SEQUENCE: 39
acatcaacaa ttttgc                                                16

<210> SEQ ID NO 40
<211> LENGTH: 17
<212> TYPE: DNA
<213> ORGANISM: Artificial Sequence
<220> FEATURE:
<223> OTHER INFORMATION: Probe

<400> SEQUENCE: 40
aacatcaact attttgc                                               17

<210> SEQ ID NO 41
<211> LENGTH: 980
<212> TYPE: DNA
<213> ORGANISM: Solanum pennellii
<220> FEATURE:
<221> NAME/KEY: misc_feature
<222> LOCATION: (72)..(225)
<223> OTHER INFORMATION: n is a, c, g, or t

<400> SEQUENCE: 41
ttgtggaaga taccactttg gatgtttata taggcaatat cgactcattc tgatgtattt    60
tgagtaggaa tnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnntcata aagttcttga   240
ttctggtgaa gagccatttg gattggacat cagttaaaga cgatgatata tcagtaatca   300
catggccctg ccttccagct agttgacatg agtaattgct ttagctcatc agatcaagtt   360
caataggtcc tgcatatatt ttcctatagg gaaccaagga tctctaagaa tcaaatccat   420
aaaaattgct ggtagcctat gatgcaaact gtgtccactt atatacaaac tataagagaa   480
wagaagtcaa aaatatgaaa gatttcactg gtggagaggt atttgttgca ctgtttattg   540
acaatagcac atgaagcatc acatggtgtt gttgccaact cattgtctaa tatatatgat   600
cttagcaaat tgctcatgaa tatcatcaga ccccagtgtt tttcatgaca agatagagaa   660
cagactatct ttagagatca aattgataat ttactgcaat agttgacaac ttgtgggatc   720
aacattccgg atgagaataa cccatggtat ttcaatagtt tttgacaagt gttttcaaat   780
agtgataaac agaaatgttt attgactatc aatatgtcta tgttttgcat atccatcaaa   840
ttatgagtca gtcagaacct tactgttgcc agaaatttga atccatattc aagaaaagta   900
tagatattat atcttattaa gagttgatga atttacatcc attttctatc tcattcagtt   960
aactcagtaa tttcacatta                                              980

<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
cctatgatgc aaactgtgtc cactt                                        25
```

```
<210> SEQ ID NO 43
<211> LENGTH: 28
<212> TYPE: DNA
<213> ORGANISM: Artificial Sequence
<220> FEATURE:
<223> OTHER INFORMATION: Primer

<400> SEQUENCE: 43
tcaataaaca gtgcaacaaa tacctctc                                           28

<210> SEQ ID NO 44
<211> LENGTH: 23
<212> TYPE: DNA
<213> ORGANISM: Artificial Sequence
<220> FEATURE:
<223> OTHER INFORMATION: Probe

<400> SEQUENCE: 44 catattttttg acttctttttc tct                                              23

<210> SEQ ID NO 45
<211> LENGTH: 23
<212> TYPE: DNA
<213> ORGANISM: Artificial Sequence
<220> FEATURE:
<223> OTHER INFORMATION: Probe

<400> SEQUENCE: 45 catattttttg acttctcttc tct                                               23

<210> SEQ ID NO 46
<211> LENGTH: 121
<212> TYPE: DNA
<213> ORGANISM: Solanum pennellii
<220> FEATURE:
<221> NAME/KEY: misc_feature
<222> LOCATION: (119)..(119)
<223> OTHER INFORMATION: n is a, c, g, or t

<400> SEQUENCE: 46
aactccctcc cctcacccga gagggcaaga tcaacaatca aatcaatctt ctttctccta        60
yggaccggtt gtttgtgccc accattcctt cctcgtcgtg aagaatctgg aagcatacnc       120
a                                                                      121

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
cgagagggca agatcaacaa tcaaa                                              25

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
ggaaggaatg gtgggcacaa a                                                  21
```

<210> SEQ ID NO 49
<211> LENGTH: 17
<212> TYPE: DNA
<213> ORGANISM: Artificial Sequence
<220> FEATURE:
<223> OTHER INFORMATION: Probe

<400> SEQUENCE: 49
caaccggtcc gtaggag                                                  17

<210> SEQ ID NO 50
<211> LENGTH: 16
<212> TYPE: DNA
<213> ORGANISM: Artificial Sequence
<220> FEATURE:
<223> OTHER INFORMATION: Probe

<400> SEQUENCE: 50
aaccggtcca taggag                                                   16

<210> SEQ ID NO 51
<211> LENGTH: 1877
<212> TYPE: DNA
<213> ORGANISM: Solanum pennellii

<400> SEQUENCE: 51
acgactgtca agagctcacc agtcgcagtt gaagcaccag cttctaaaga gttaggtgtt     60
caagcaggag tctatggagc cttaatggtc ttaacatatg ttaatggagc ctcaacacct    120
ttaggagtat cgtatggagc tgatgttcct ggactaatct tagccacaag ctttggggcc    180
accttgtact tcatgaccaa gaaaaatgtc aagttgggta aggaagatac gttgcttctc    240
tttgtttcac ttctaggtag atttattgca ttttgtgagt tcaaatataa acattagtac    300
gtgattgcag tcatgcaaaa gtaatgacca aattgtttgt taaagtatat aatagccccc    360
catatacgtg ttaagtttgc tcattgacat tccatactaa ctgaatctta agcattatct    420
ctggatcact taagctttca caatttcaac ttaccctcaa gaaaaccata gctagggttg    480
taatccctta tcatatgcat ttctaacctt gtgagaaaaa tagacttgac ttgatgctca    540
tgctagtatc cataaaatct ttttggcgtg taagaagtgt ctttctcatc aacaattatg    600
aacataattc acagattttc ctgtgttgct aaatcatttt tttttcttaa ttaataggac    660
tggattattg tcaatagttg aatgtgtttc ttctaattag ttatggatcc atgtctttta    720
tcacgttgat aatgaacaaa cattttggtc ttcaactcct taatactccc attaaatcta    780
agttgtcgac tatttgatga agacttactt gaatatttcc tattatacaa aaaaactacg    840
tgatggtttg atttgatgag agttattaag gtgagaatta ggaatacgta tcatgcaatg    900
taaatatgga agaagcttgt catgtataca ctggttcgtc aagtgttatg aactgaagaa    960
gtgtttcagt acaattattt gaagaaatat ataaaaaaag gatcacatta tatgtaggga   1020
agatcacatt atacaaattt tccatgttgc tgaagtggaa atcattctaa ggttgtggag   1080
agtggagacc atgatttatt tatttttaatt gaaaacaagt ttatataatc cttatctatc   1140
atatgaaaat gacatgagta gtagccacat aagagccaat gaaattttga aggagttgat   1200
ttgtgtggaa gtactgttct ggcttctgga taatgcaaat gagactttgg aaataccaac   1260
aatggatttg taccgtgtta tgattccgat tagtgtttat ttcatctaag ctgtatttct   1320
gccaaaaaaa tatttgtaga actaaatatt ggctttccct gaaaaaaatg actcaaactt   1380
tacttgcaaa caggaaagc aagcgtcata acaattggtg ggctggtcgc tggtgcagtg    1440

```
gtaggttcag cagtagaaaa ttggttgcaa gtagacattg tcccgttact gggtatacac    1500
actcctgcta cggttgtgag tgaatttata cttttctcgc aatttctggt ctcgttgtat    1560
ctgatatagg gtaactcaaa ggcttgtatg arctgctact gtaagaaggt ctatggctat    1620
ttgttgccta ctcaggttct tgttcttatc taggaccagt aatttgttaa atgtacaaaa    1680
gaatgttacc aaaactctgg aagttctgat atttgtttta taaagctagt atagattctc    1740
agctttgctc ttctatcaac ggtattttaa tccctagttt gttctgatat taagttgtgg    1800
cttactgtgt tttaattgga atttgacgta tttattttct cacagaaggg tacattgatt    1860
ataacaggct tggactc                                                   1877
```

```
<210> SEQ ID NO 52
<211> LENGTH: 28
<212> TYPE: DNA
<213> ORGANISM: Artificial Sequence
<220> FEATURE:
<223> OTHER INFORMATION: Primer

<400> SEQUENCE: 52
gcaatttctg gtctcgttgt atctgata                                         28

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
cctgagtagg caacaaatag ccata                                            25

<210> SEQ ID NO 54
<211> LENGTH: 20
<212> TYPE: DNA
<213> ORGANISM: Artificial Sequence
<220> FEATURE:
<223> OTHER INFORMATION: Probe

<400> SEQUENCE: 54
cttacagtag cagttcatac                                                  20

<210> SEQ ID NO 55
<211> LENGTH: 17
<212> TYPE: DNA
<213> ORGANISM: Artificial Sequence
<220> FEATURE:
<223> OTHER INFORMATION: Probe

<400> SEQUENCE: 55
acagtagcag ctcatac                                                     17

<210> SEQ ID NO 56
<211> LENGTH: 601
<212> TYPE: DNA
<213> ORGANISM: Solanum pennellii
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
```

```
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t

<400> SEQUENCE: 56
cattttggat ccacttctgg tgaaaagggt aagtttgggt tgacaacaac ccagattctt      60
cgtgtagtga agaagcttga tgaatctgga atgctggatt gtctccagtt attgcatttt     120
cacattggat ctcagatccc cacaacagag ttgcttgctg atggtgttgg tgaggccact     180
cagatttact ctgaattagt ccgtcttgga gctggtatga aattcattga tatcggaggg     240
gggcttggaa tcgactatga cggttctaaa tcaagcaatt ctgatgtctc tgttngctat     300
rgcattgaag aatatgcctc tgctgttgtc caagcggtcc tctatgtctg tgatcgtaag     360
ggcgtaaagc atccagtgat ttgcagcgaa agtggcaggg caattgtttc tcaccattca     420
attctgattt ttgaagccgt gtctgcttct actantcatg tttctacnca gccatcttcg     480
ggtggtttac aatccttggt ggagactctc aatgaagatg cccgtgctga ctacngaaac     540
ttatctgctg ctgctgtccg tggagaatat gatacatgtc tcatctattc tgatcanttg     600
a                                                                     601

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
cgactatgac ggttctaaat caagca                                           26

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
aggaccgctt ggacaacag                                                   19

<210> SEQ ID NO 59
<211> LENGTH: 21
<212> TYPE: DNA
<213> ORGANISM: Artificial Sequence
<220> FEATURE:
<223> OTHER INFORMATION: Probe

<400> SEQUENCE: 59
catattcttc aatgctatag c                                                21

<210> SEQ ID NO 60
<211> LENGTH: 20
<212> TYPE: DNA
<213> ORGANISM: Artificial Sequence
<220> FEATURE:
<223> OTHER INFORMATION: Probe
```

<400> SEQUENCE: 60
atattcttca atgccatagc                                            20

<210> SEQ ID NO 61
<211> LENGTH: 601
<212> TYPE: DNA
<213> ORGANISM: Solanum lycopersicum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:

```
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t

<400> SEQUENCE: 61
caaatctctt cttctgcttt tccccaacat aaacagcnaa gtggccttta ggaacatctc    60
cggttgtgga agacttcntg attatacgag ncatanggat agccatggtc ntttagttca   120
atataagatg agaaaatnag gatgngnaga attagtaaag actctgaaac cagagaaagn   180
tttgtatggt ttcaaatttt gctgagtgtt gttgcagtaa ccccttnttt ntatgtgttt   240
atataggcta atatcaagtn gtagaattct actgatgtgc attgaataga cattatgtgg   300
kcaccagcta aaggcantag cacctgaagt atcacatggt tttgccttnc aactcattct   360
cataatataa atacaatgaa agtagtctna aatcagaagg tcctantgat nttcacaacn   420
aataacagat ggaaatttta tacttcttga naaatggttt agcttcttga tgttaaatca   480
acaagtaata gtcagattcc aatgattgat caaccaccag acaccaatng nacaaagaaa   540
agtgggatgt tccagccttc cagatgctga attcaatcct aaatatcaag aatatcacaa   600
t                                                                  601

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gctgagtgtt gttgcagtaa cc                                             22

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
aaggcaaaac catgtgatac ttcag                                          25

<210> SEQ ID NO 64
<211> LENGTH: 17
<212> TYPE: DNA
<213> ORGANISM: Artificial Sequence
<220> FEATURE:
<223> OTHER INFORMATION: Probe

<400> SEQUENCE: 64
attatgtggg caccagc                                                   17

<210> SEQ ID NO 65
<211> LENGTH: 18
```

```
<212> TYPE: DNA
<213> ORGANISM: Artificial Sequence
<220> FEATURE:
<223> OTHER INFORMATION: Probe

<400> SEQUENCE: 65
cattatgtgg tcaccagc                                                       18
```